United States Patent
Shah et al.

(10) Patent No.: US 12,150,692 B2
(45) Date of Patent: Nov. 26, 2024

(54) SIMULTANEOUS ELECTROSURGICAL SEALING AND CUTTING

(71) Applicant: Intuitive Surgical Operations, Inc., Sunnyvale, CA (US)

(72) Inventors: Jignesh M. Shah, Sunnyvale, CA (US); Jason W. Hemphill, Los Gatos, CA (US); Forrest R. Lundstrom, Sunnyvale, CA (US); Duane W. Marion, Scottsdale, AZ (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 424 days.

(21) Appl. No.: 16/956,492

(22) PCT Filed: Dec. 19, 2018

(86) PCT No.: PCT/US2018/066575
§ 371 (c)(1),
(2) Date: Jun. 19, 2020

(87) PCT Pub. No.: WO2019/126370
PCT Pub. Date: Jun. 27, 2019

(65) Prior Publication Data
US 2021/0093369 A1    Apr. 1, 2021

Related U.S. Application Data
(60) Provisional application No. 62/607,817, filed on Dec. 19, 2017.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1442* (2013.01); *A61B 2017/00154* (2013.01);
(Continued)

(58) Field of Classification Search
CPC ............ A61B 18/1206; A61B 18/1442; A61B 2018/124; A61B 2018/1452
See application file for complete search history.

(56) References Cited

U.S. PATENT DOCUMENTS 3,699,967 A * 10/1972 Anderson .......... A61B 18/1206
128/DIG. 22
5,558,671 A    9/1996 Yates
(Continued)

FOREIGN PATENT DOCUMENTS

CN    1750794 A    3/2006
CN    103025259 A    4/2013
(Continued)

OTHER PUBLICATIONS

Extended European Search Report for Application No. EP18892352.8 mailed on Aug. 26, 2021, 10 pages.
(Continued)

*Primary Examiner* — Daniel W Fowler
(74) *Attorney, Agent, or Firm* — Artegis Law Group, LLP

(57) ABSTRACT

A method is provided to seal and cut biological tissue. An alternating current (AC) scaling signal is imparted between a set of sealing electrodes. An AC cutting signal is imparted between a set of cutting electrodes in response to a biological tissue impedance between the sealing electrodes reaching a first impedance threshold value. The AC scaling signal is halted at an end of a time interval, beginning while the AC cutting signal is imparted between the cutting electrodes, in
(Continued)

response to impedance of the biological tissue disposed between the set of sealing electrodes reaching a second impedance threshold value.

21 Claims, 11 Drawing Sheets

(51) Int. Cl.
    A61B 17/00    (2006.01)
    A61B 18/00    (2006.01)
    A61B 34/35    (2016.01)

(52) U.S. Cl.
    CPC .............. *A61B 2018/00601* (2013.01); *A61B 2018/0063* (2013.01); *A61B 2018/00654* (2013.01); *A61B 2018/00666* (2013.01); *A61B 2018/00708* (2013.01); *A61B 2018/0072* (2013.01); *A61B 2018/00755* (2013.01); *A61B 2018/1452* (2013.01); *A61B 34/35* (2016.02)

(56) References Cited

U.S. PATENT DOCUMENTS

| | | | |
|---|---|---|---|
| 5,702,390 A * | 12/1997 | Austin | A61B 18/1445 606/41 |
| 6,152,923 A * | 11/2000 | Ryan | A61B 18/1445 606/42 |
| 8,357,151 B2 | 1/2013 | Goldberg et al. | |
| 8,740,901 B2 | 6/2014 | Johnson et al. | |
| 9,375,262 B2 | 6/2016 | Reschke et al. | |
| 2002/0058933 A1 | 5/2002 | Christopherson et al. | |
| 2003/0069571 A1 | 4/2003 | Treat et al. | |
| 2004/0116922 A1 | 6/2004 | Hovda et al. | |
| 2005/0096681 A1 * | 5/2005 | Desinger | A61B 18/1402 606/50 |
| 2006/0095031 A1 | 5/2006 | Ormsby | |
| 2007/0250052 A1 * | 10/2007 | Wham | A61B 18/1206 606/34 |
| 2008/0058802 A1 * | 3/2008 | Couture | A61B 18/1442 606/51 |
| 2008/0294156 A1 | 11/2008 | Newton et al. | |
| 2010/0137854 A1 | 6/2010 | Hosier | |
| 2010/0241116 A1 * | 9/2010 | Benamou | A61B 18/18 606/33 |
| 2010/0292691 A1 * | 11/2010 | Brogna | A61B 18/1445 606/45 |
| 2011/0015631 A1 | 1/2011 | Wiener et al. | |
| 2011/0306959 A1 * | 12/2011 | Kellerman | A61B 17/11 606/28 |
| 2012/0116391 A1 * | 5/2012 | Houser | A61B 34/76 606/1 |
| 2012/0239024 A1 * | 9/2012 | Ladtkow | A61B 18/1206 606/34 |
| 2014/0031815 A1 * | 1/2014 | Miersch | A61B 18/1206 606/48 |
| 2014/0066913 A1 * | 3/2014 | Sherman | A61B 18/1492 606/41 |
| 2014/0180281 A1 * | 6/2014 | Rusin | A61B 18/1442 606/49 |
| 2014/0277049 A1 * | 9/2014 | Rethy | A61B 18/1445 606/180 |
| 2014/0353869 A1 * | 12/2014 | Goodman | A61B 18/1445 264/104 |
| 2015/0066022 A1 | 3/2015 | Shelton, IV et al. | |
| 2015/0282867 A1 * | 10/2015 | Keller | A61B 18/1445 606/52 |
| 2016/0045248 A1 | 2/2016 | Unger et al. | |
| 2016/0066980 A1 * | 3/2016 | Schall | A61B 18/1442 606/45 |
| 2016/0249975 A1 * | 9/2016 | Konishi | A61B 18/1445 606/45 |
| 2016/0346034 A1 * | 12/2016 | Arya | A61B 18/22 |
| 2017/0065331 A1 | 3/2017 | Mayer et al. | |
| 2017/0164998 A1 | 6/2017 | Klimovitch | |

FOREIGN PATENT DOCUMENTS

| | | |
|---|---|---|
| CN | 103237512 A | 8/2013 |
| CN | 104363842 A | 2/2015 |
| CN | 106163437 A | 11/2016 |
| EP | 2076195 A1 | 7/2009 |
| GB | 2480498 A | 11/2011 |
| JP | 2010527676 A | 8/2010 |
| JP | 2013542765 A | 11/2013 |
| JP | 2016154908 A | 9/2016 |
| JP | 2017521188 A | 8/2017 |
| KR | 20170016403 A | 2/2017 |
| WO | WO-2011144911 A1 | 11/2011 |
| WO | WO-2015094493 A1 | 6/2015 |
| WO | WO-2015184446 A2 | 12/2015 |
| WO | WO-2017053945 A1 | 3/2017 |

OTHER PUBLICATIONS

International Search Report and Written Opinion for Application No. PCT/US2018/066575, mailed on Apr. 16, 2019, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action for Chinese Application No. CN20188081514.0, mailed Nov. 8, 2022, 20 pages.
Notice of Preliminary Rejection for Korean Application No. 1020227032355, mailed on Jun. 7, 2023, 05 pages.
Notification of Reasons for Refusal of Japanese Application No. 2021188113, mailed on Feb. 14, 2023, 16 pages.

* cited by examiner

SIMULTANEOUS ELECTROSURGICAL SEALING AND CUTTING

CLAIM OF PRIORITY

This application is a U.S. National Stage Filing under 35 U.S.C. 371 from International Application No. PCT/US2018/066575, filed on Dec. 19, 2018, and published as WO 2019/126370 A1 on Jun. 27, 2019, which claims the benefit of priority to U.S. Provisional Patent Application No. 62/607,817, entitled "ELECTROSURGICAL SYSTEM AND METHOD TO SIMULTANEOUSLY SEAL AND CUT," filed on Dec. 19, 2017, each of which is incorporated by reference herein in its entirety.

BACKGROUND

Electrosurgery involves the use of electricity to buildup heat within biological tissue to cause thermal tissue damage resulting in incision, removal or sealing of the tissue through one or more of desiccation, coagulation, or vaporization, for example. Benefits include the ability to make precise cuts with limited blood loss. Electrosurgical devices are frequently used during surgical procedures to help prevent blood loss in hospital operating rooms or in outpatient procedures. High-frequency electrosurgery typically involves radio frequency (RF) alternating current (AC) that is converted to heat by resistance as it passes through the tissue.

A typical electrosurgical signal generator uses a multi-stage voltage converter to convert AC line power to a controlled high frequency signal required to perform an electrosurgical procedure. This approach ordinarily includes converting an AC line input to direct current (DC) signal and converting the DC signal to an RF signal. The RF output is imparted to electrodes at a surgical instrument end effector that a surgeon manipulates to impart high frequency energy to seal or cut anatomical tissue.

A previous electrosurgical instrument has been provided that includes an end effector for both sealing and cutting vessels and/or tissue. The prior end effector includes a pair of opposing first and second jaws that are movable relative to one another from a first spaced apart position to a second position for grasping tissue therebetween. Each jaw includes an electrically conductive tissue sealing surface configured to be energized by an electrosurgical energy source and configured to contact a tissue surface. At least one of the jaws includes an electrically conductive cutting surface disposed within an insulator defined in the jaw. The cutting surface is configured to be energized by an electrosurgical energy source and is configured to contact a tissue surface.

SUMMARY

In one aspect, a method is provided to seal and cut biological tissue. An alternating current (AC) sealing signal is imparted between a set of sealing electrodes. An AC cutting signal is imparted between a set of cutting electrodes in response to biological tissue impedance between the sealing electrodes reaching a first impedance threshold value. The AC sealing signal is halted at an end of a time interval, beginning while the AC cutting signal is imparted between the cutting electrodes, in response to impedance of biological tissue disposed between the set of sealing electrodes reaching a second impedance threshold value.

In another aspect, an electrosurgical system is provided. An electrosurgical signal generator sealing stage is configured to provide an AC sealing signal on a set of sealing electrodes. An electrosurgical signal generator cutting stage is configured to provide an AC cutting signal on a set of cutting electrodes. The set of sealing electrodes and the set of cutting electrodes share at least one electrode in common.

DESCRIPTION OF EMBODIMENTS

Teleoperated Surgical System

Figure 1:
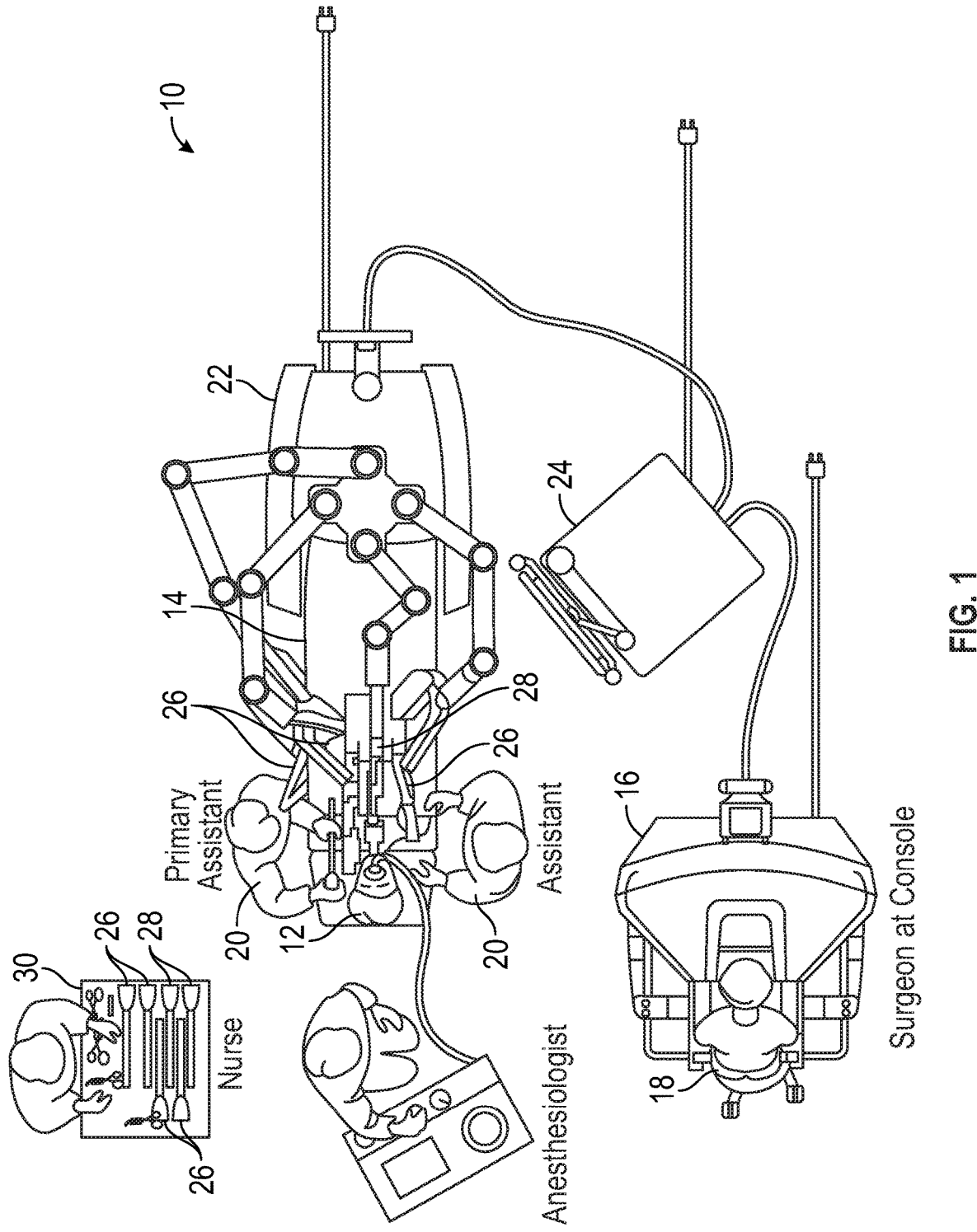
FIG. 1 is an illustrative plan view of a minimally invasive teleoperated surgical system for performing a minimally invasive diagnostic or surgical procedure on a patient who is lying on an operating table.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes one or more patient-side cart 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
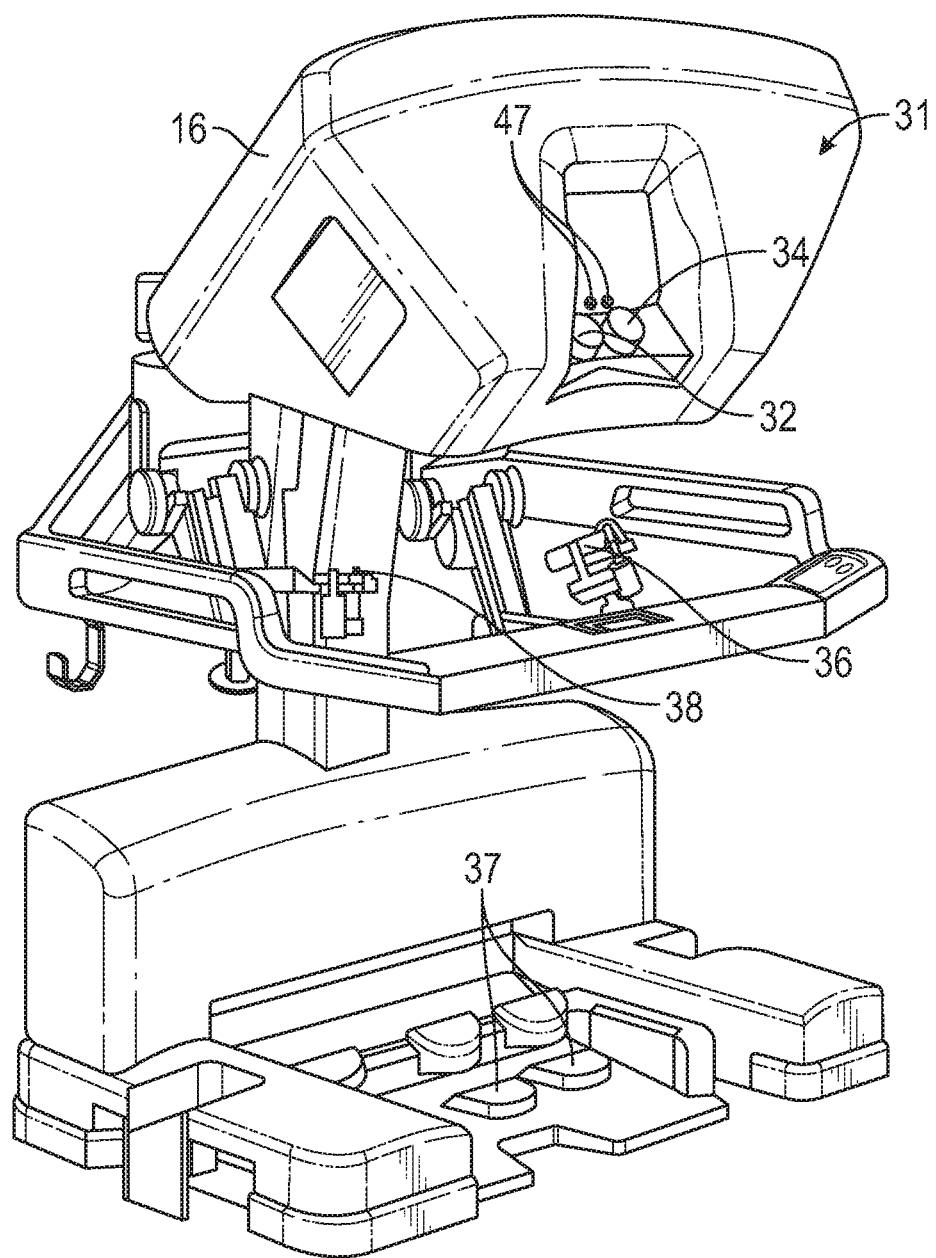
FIG. 2 is an illustrative perspective view of the surgeon's console.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive the larger-scale hand control movements and includes one or more foot pedal controls 37. One or more surgical instruments installed for use on the patient-side cart 22 move in smaller-scale distances in response to surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
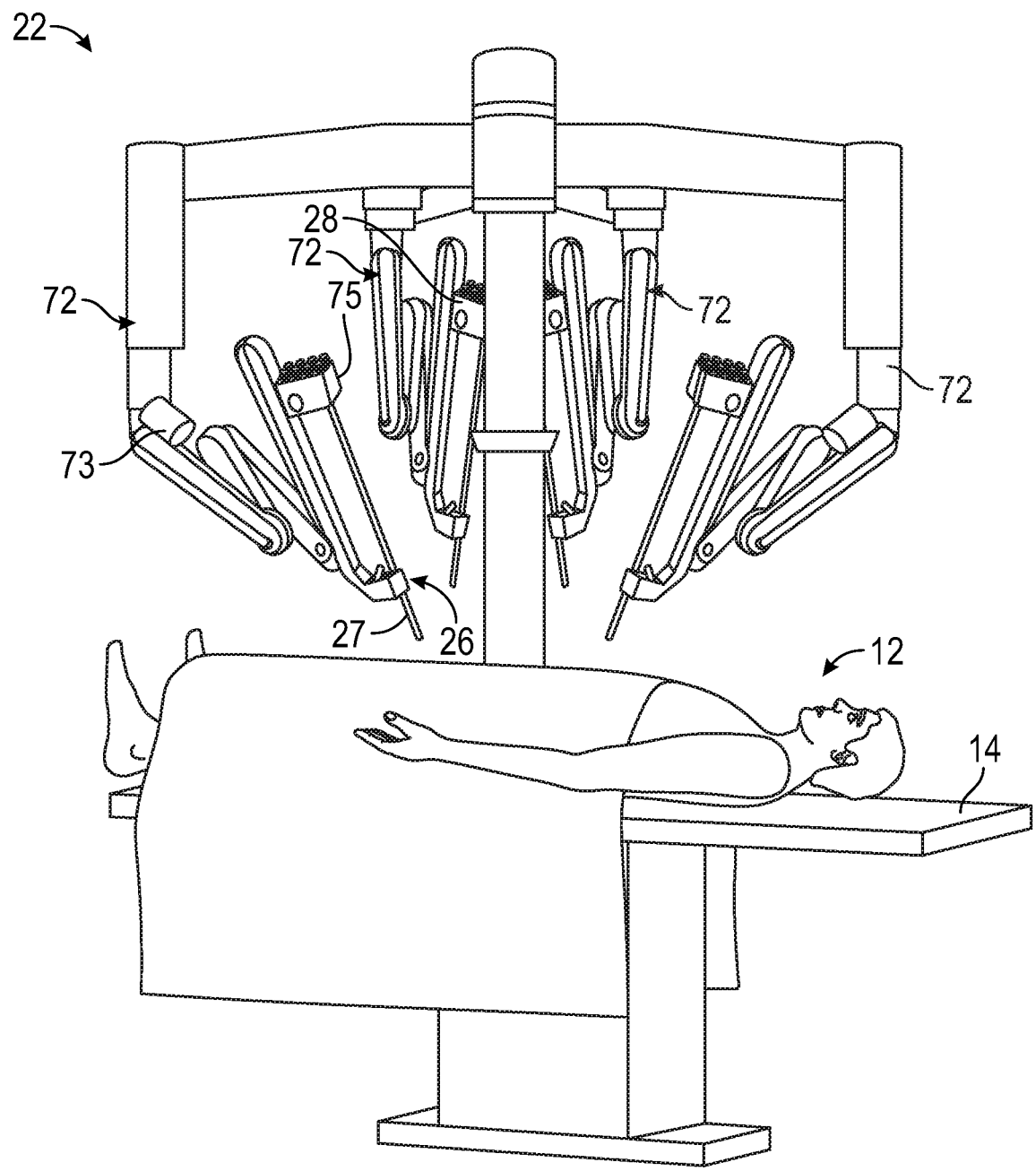
FIG. 3 is an illustrative perspective view of a patient-side cart of a minimally invasive teleoperated surgical system.

FIG. 3 is a perspective view of a patient-side cart 22 of a minimally invasive teleoperated surgical system 10, in accordance with embodiments. The patient-side cart 22 includes four mechanical support arms 72. A surgical instrument manipulator 73, which includes motors to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 22 is shown as including four surgical instrument manipulators 73, more or fewer surgical instrument manipulators 73 may be used. A teleoperated surgical system will generally include a vision system that typically includes an endoscopic camera instrument 28 for capturing video images and one or more video displays for displaying the captured video images. User inputs provided at the control console 16 to control either the instrument as a whole or the instrument's components are such that the input provided by a surgeon or other medical person to the control input (a "master" command) is translated into a corresponding action by the surgical instrument (a "slave" response).

Figure 4:
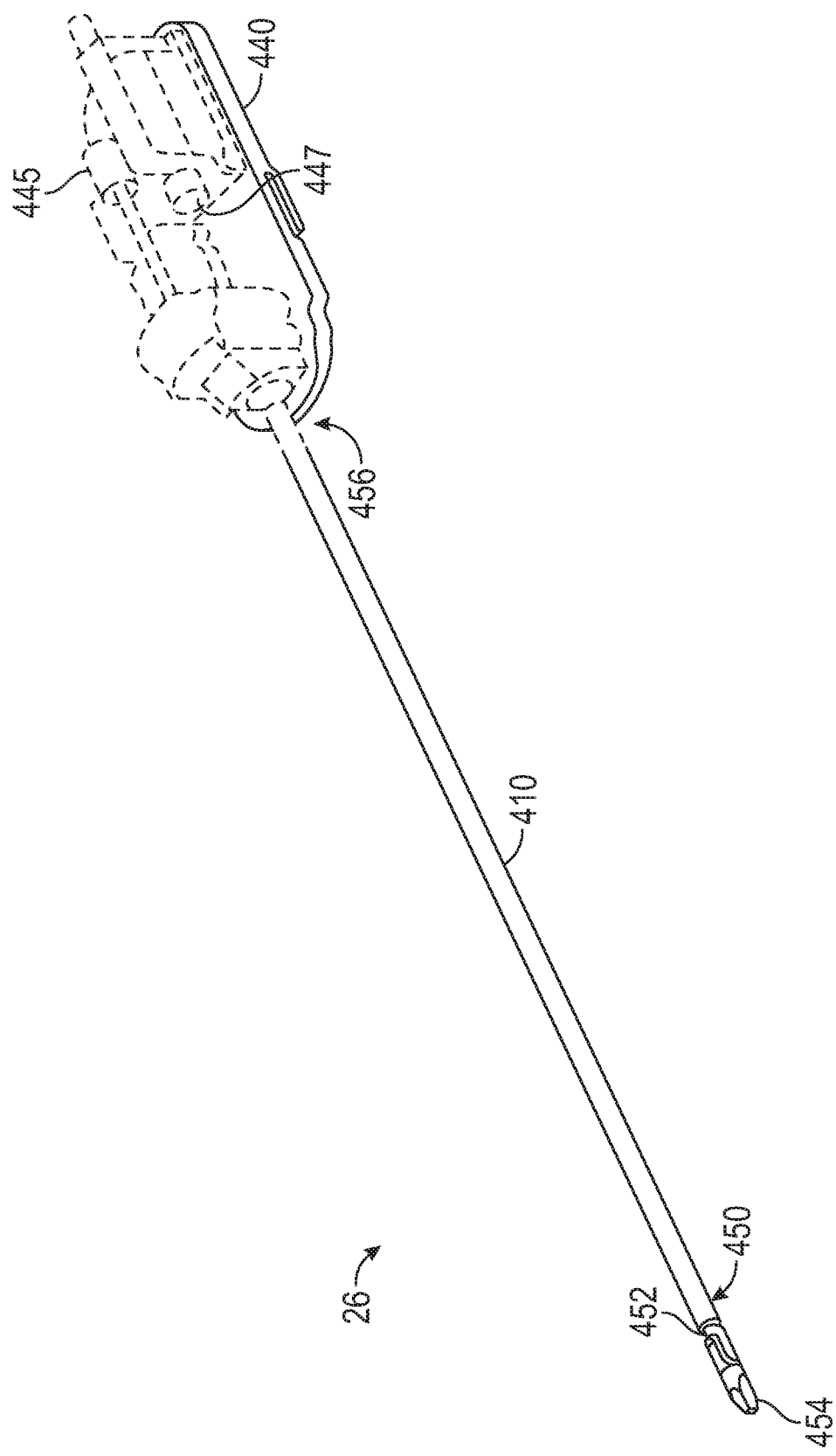
FIG. 4 is an illustrative perspective view of a surgical instrument.

FIG. 4 is a perspective view of a surgical instrument 26, which includes an elongated hollow tubular shaft 410 having a centerline longitudinal axis 411, a distal (first) end portion 450 for insertion into a patient's body cavity and proximal (second) end portion 456 coupled adjacent a control mechanism 440 that includes multiple actuator motors 445, 447 (shown with dashed lines) that exert force upon wire cables coupled to impart motion to the end effector 454 such as opening or closing of jaws and (x, y) wrist motion of a wrist. The surgical instrument 26 is used to carry out surgical or diagnostic procedures. The distal portion 450 of the surgical instrument 26 can provide any of a variety of end effectors 454, such as the forceps shown, a needle driver, a cautery device, a cutting tool, an imaging device (e.g., an endoscope or ultrasound probe), or the like. The surgical end effector 454 can include a functional mechanical degree of freedom, such as jaws that open or close, or a knife that translates along a path or a wrist that may move in x and y directions. In the embodiment shown, the end effector 454 is coupled to the elongated hollow shaft 410 by a wrist 452 that allows the end effector to be oriented relative to the elongate tube centerline axis 411. The control mechanism 440 controls movement of the overall instrument and the end effector at its distal portion.

Electrosurgical Signal Generator

Figure 5:
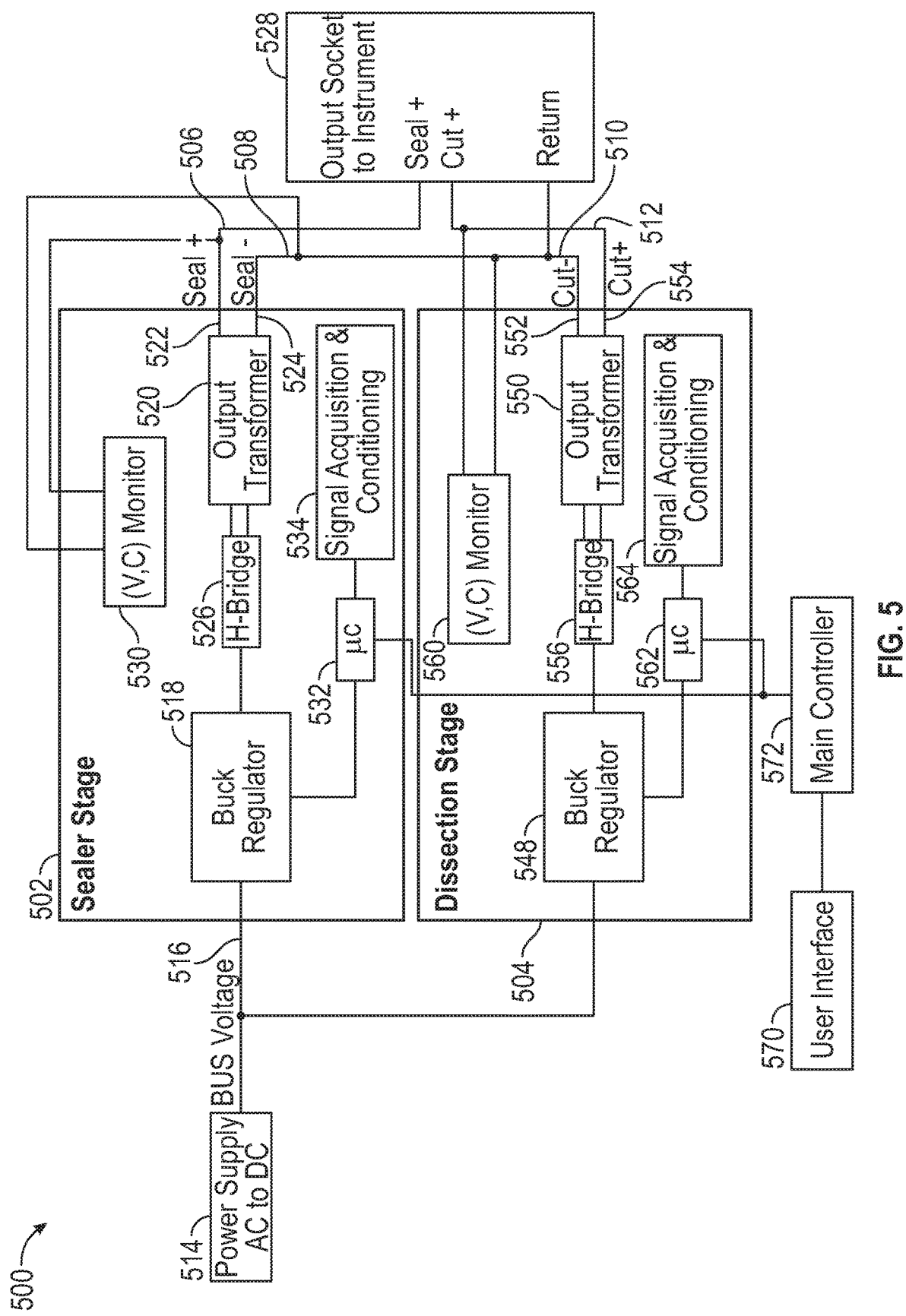
FIG. 5 is an illustrative block diagram representing an electrosurgical signal generator circuit in accordance with some embodiments.

FIG. 5 is an illustrative block diagram representing an electrosurgical signal generator circuit 500 in accordance with some embodiments. The electrosurgical signal generator 500 includes an electrosurgical signal generator sealing stage 502 and an electrosurgical signal generator cutting stage 504. The sealing stage 502 produces a high frequency (HF) AC sealing signal between a set of sealing electrodes 506, 508 (seal+, seal−). The cutting stage 504 produces a HF AC cutting signal between a set of cutting electrodes 510, 512 (cut+, cut−). Typically, the frequency is in a range of approximately 100-500 kHz. In some embodiments, the set of sealing stage electrodes 506, 508 and the set of cutting stage electrodes 510, 512 each shares at least one electrode 508, 512 (seal−, cut−) in common, which may be referred to collectively herein as the return electrode.

The electrosurgical signal generator 500 includes an AC-to-DC power supply 514 to convert an AC line voltage to a DC voltage on a voltage bus line 516. The voltage bus line 516 is coupled to provide a DC input voltage signal to the sealing stage circuit 502. The voltage bus line 516 also is coupled to provide the DC input voltage signal to the cutting stage circuit 504. In some embodiments, the DC input voltage signal is approximately 48V, for example.

The sealing stage 502 includes a first buck regulator circuit 518 to convert the DC input voltage signal to a first controlled DC voltage signal and includes a first output transformer 520 coupled to produce the AC sealing signal based upon the first controlled DC voltage signal. The first output transformer 520 is coupled to provide the sealing signal to the set of sealing electrodes 506, 508. More particularly, the first output transformer 520 includes a first terminal 522 electrically coupled to the first sealing electrode 506 and includes a second terminal 524 electrically coupled to the second sealing electrode 508. The first controlled DC voltage signal is provided to a first output stage 526, which is configured to provide the first controlled voltage across the terminals 522, 524 of the first output transformer 520 in either polarity direction. In some embodiments, the first output stage includes a first H-bridge switch circuit. The first and second sealing electrodes 506, 508 are electrically coupled via an output socket 528 to a surgical instrument end effector 454, which includes a jaw end effector described below with reference to FIGS. 6A-6B. A first voltage and current monitoring circuit 530 is configured to monitor current and voltage across the set of sealing electrodes. A first micro-controller 532 is configured to provide a pulse width modulated (PWM) signal to the first buck regulator circuit 518 to determine the voltage conversion imparted by the first buck regulator circuit 518.) The first micro-controller 532 also is configured to produce a control signal to control switching of the output stage switch circuit 526 to thereby determine the HF sealing signal waveform pattern, including duty cycle and frequency, for example. First signal conditioning and acquisition circuitry 534 acquire the voltage and current measurements used to calculate RMS V, I; and average power. The first micro-controller 532 also is configured to determine a first impedance between the set of sealing electrodes 506, 508 based upon the monitored voltage and current across them.

Similarly, the cutting stage 504 includes a second buck regulator circuit 548 to convert the DC input voltage signal to a second controlled DC voltage signal and includes a second output transformer 550 coupled to produce the cutting signal based upon the second controlled DC voltage signal. The second output transformer 550 is coupled to provide the AC cutting signal to the set of cutting electrodes 510, 512. More specifically, the second output transformer 550 includes a first terminal 552 electrically coupled to the first cutting electrode 510 and includes a second terminal 554 electrically coupled to the second cutting electrode 512. The second controlled DC voltage signal is provided to a second output switching circuit 556, which is configured to provide the second controlled voltage across the terminals 552, 554 of the second output transformer 550 in either polarity direction. The set of cutting electrodes 510, 512 are electrically coupled via the output socket 528 to the surgical instrument end effector 454, which includes a jaw end effector described below with reference to FIGS. 6A-6B. A second current and voltage monitoring circuit 560 is configured to monitor current and voltage across the set of cutting electrodes 510, 512. A second micro-controller 562 is configured to provide a pulse width modulated (PWM) signal to the second buck regulator circuit 548 to determine the voltage conversion imparted by the second buck regulator circuit 548. The second micro-controller 562 also is configured to produce a control signal to control switching of the output stage switching circuit 556 to thereby determine the cutting? signal waveform pattern, including duty cycle and frequency, for example. Second signal conditioning and acquisition circuitry 564 acquire the voltage and current measurements used to calculate RMS V, I; and average power. The second micro-controller 562 also is configured to determine a second impedance between the set of cutting electrodes 510, 512 based upon the monitored voltage and current across them.

A user interface circuit (UI) block 570, which may be incorporated in the control console 16, may include one or more of hand controls and foot pedal controls and a display console to receive user input commands to start and stop sealing and cutting activities and to indicate parameters to use for scaling and cutting signal waveforms such as voltage, current, signal frequency, and dwell time, for example. The UI circuit block 570 also may provide feedback information to the user such as amount of power delivered, whether a seal was successfully completed, whether an error condition occurred. A surgeon may use the UI to provide user input to select voltage and current levels or sealing signal patterns and cutting signal patterns based upon requirements of a particular patient or surgical procedure, for example. A main controller 572, which may be incorporated in the electronics cart 24, is coupled to exchange information with the UI block 570 and to communicate with the first and second micro-controllers 532, 562. The main controller 572 may be configured to produce control signals to determine waveforms of the scaling and cutting signals under control of the first and second micro-controllers, including current and voltage levels, for example. The main controller 572 also may produce control signals to determine start and stop times of sealing and cutting operations under control of the first and second micro-controllers. In some embodiments, the main controller 572 also may be configured to provide control signals to the first and second micro-controllers for arc suppression and other time dependent functions. Values may change, for example, as a function of user settings or depending on what happens in the other stage.

In operation, an AC sealing signal is provided via the first output transformer 520 across the set of sealing electrodes 506, 508, and an AC cutting signal is provided via the second output transformer 550 across the set of cutting electrodes 510, 512. In some embodiments, the first and second micro-controllers 532, 562 cooperate to provide a single PWM master signal to the first and second H-bridge switches 526, 556 to produce in-phase periodic sealing and cutting signals. Although the sealing and cutting signals are periodic signals that are in phase with each other, they typically have different peak-to-peak voltage potentials. The first and second output transformers 520, 550 may have different turn ratios to produce different voltage levels for the sealing and cutting voltages, for example. In general, impedance is lower during a sealing activity than during a cutting activity due to the higher impedance associated with the plasma discharge required to resect tissue. Thus, in general, a lower voltage ordinarily may be used during sealing than is used during a cutting. In some embodiments, for example, the peak-to-peak voltage for a sealing activity is approximately 75-150V and the peak-to-peak voltage for a cutting activity is approximately 300-600V. Conversely, in general, a higher current may be used during sealing than is used during a cutting.

Figure 6A:
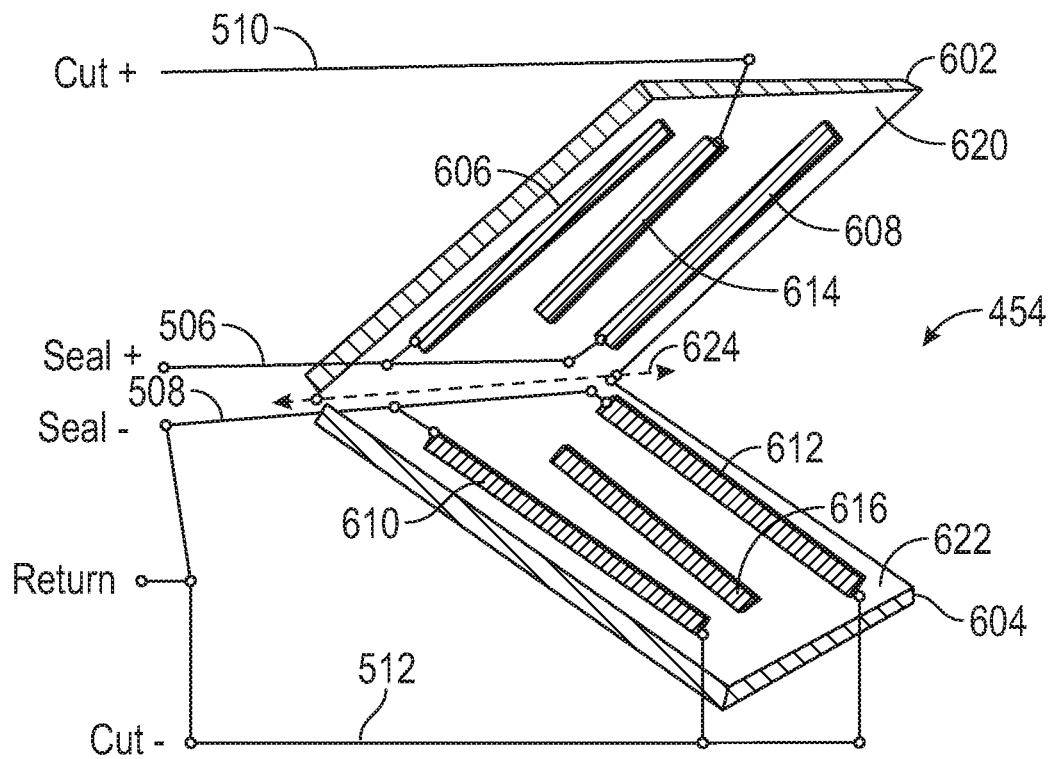
FIG. 6A is an illustrative perspective view of a pair of jaws of an end effector that include a set of tissue sealing surfaces and a set of tissue cutting surfaces shown in an open position in accordance with some embodiments.
Figure 6B:
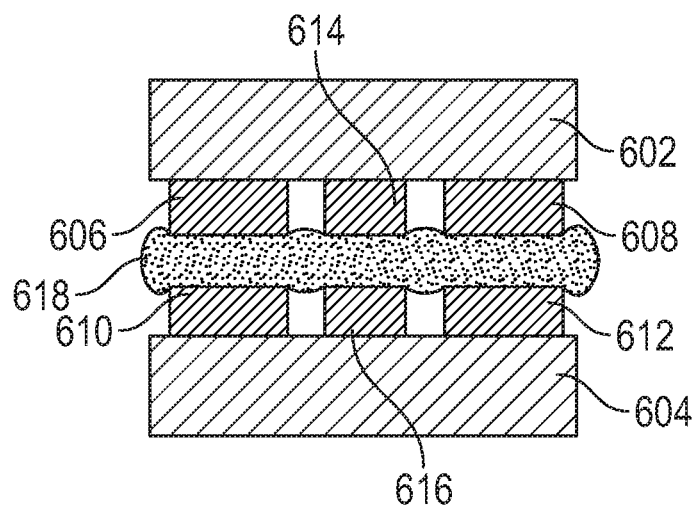
FIG. 6B is a distal end view of the pair of end effector jaws of FIG. 6A shown in a closed position with biological tissue grasped between them in accordance with some embodiments.

FIG. 6A is an illustrative perspective view of a pair of jaws 602, 604 of an end effector 454 that include a set of tissue sealing surfaces 606-612 and a set of tissue cutting surfaces 610, 612 and 614 shown in an open position in accordance with some embodiments. Thus, sealing surfaces 610, 612 are shared between the sealing stage 502 and the cutting stage 504. FIG. 6B is a distal end view of the pair of end effector jaws 602, 604 of FIG. 6A shown in a closed position with biological tissue 618 grasped between them in accordance with some embodiments. Referring to FIG. 6A, the end effector 454 includes first and second jaws 602, 604 having opposing working faces 620, 622 and a pivot axis 624. At least one of the first and second jaws 602, 604 is mounted to rotatably pivot about the pivot axis 624 between the open position in which the first and second jaws 602, 604 are spaced apart from each other and the closed position for grasping biological tissue 618 between them.

The first jaw 602 includes first and second electrically conductive tissue sealing surfaces 606, 608 that are electrically coupled at the socket 528 to the active sealing electrode 506 and that extend longitudinally along outer portions of the first jaw 602. The first jaw 602 also includes an electrically conductive tissue cutting surface 614 that is electrically coupled at the socket 528 to the active cutting electrode 510 and that extends longitudinally along the first jaw 602 between the first and second tissue sealing surfaces 606, 608. The second jaw 604 includes third and fourth electrically conductive tissue sealing surfaces 610, 612 that are electrically coupled at the socket 528 to the shared return sealing electrode 508 and that extend longitudinally along outer portions of the second jaw 604 so as to align with the first and second tissue sealing surfaces 606, 608 when the first and second jaws 602, 604 are in the closed position. The second jaw 604 also includes a passive/insulative surface 616 that extends longitudinally along the second jaw 604 between the third and fourth tissue sealing surfaces 610, 612 so as to align with the first tissue cutting surface 614 when the first and second jaws 602, 604 are in the closed position.

Referring to FIG. 6B, during tissue sealing activity, the sealing signal is conducted through tissue portion 618 disposed between the first and third sealing surfaces 606, 610 and through tissue portion 618 disposed between the second and fourth tissue sealing surfaces 608, 612. During tissue cutting, the cutting signal is conducted though a tissue portion 618 disposed between the first and second tissue cutting surfaces 610, 612, 614. Often, it is beneficial to start a sealing activity before a cutting activity for reduced clinical risk. In this way, if biological tissue, such as a blood vessel, is sealed to some pre-determined extent before cutting begins, there is minimal risk of blood leakage during a later-started cutting activity.

In general, the voltage and current density applied to a biological tissue determines whether cutting or sealing of the tissue occurs, as a higher voltage and current density is required to achieve the plasma discharge required for resection. A lower current density typically results in less rapid tissue heating, which may result in sealing, which as used herein, refers to tissue dehydration, vessel wall shrinkage and coagulation of blood constituents and collagen denaturalization and bonding. A higher current density typically results in the creation of a plasma discharge, which may result in cutting, which as used herein, refers to dissecting of tissue through vaporization, for example. Although electrosurgical sealing signals and electrosurgical cutting signals may deliver the same power, they ordinarily use different voltage and current levels to do so.

A typical electrosurgical procedure that involves both sealing and cutting activities may involve a sequence of "bites" in which a pair of jaws grasp a tissue portion, the electrosurgical generator provides sealing and cutting signals to seal it and cut it, and then a next portion of tissue is grasped, sealed and cut, etc. Each bite of sealing activity and each cutting activity may require only a short time interval, such as two seconds to seal and two seconds to cut, for example. The overall time required for an electrosurgical procedure increases with an increasing number of bites. For example, an electrosurgical procedure involving 5-6 bites in which sealing and cutting activities are performed in sequence may require 20-24 seconds. Moreover, if a single stage electrosurgical generator is used, then an additional time delay of perhaps 4-5 seconds per bite may be required, for example, to reconfigure the generator to generate a different signal pattern at each transition between a sealing and a cutting activity, which can further increase the overall time for an electrosurgical procedure by an additional 20-30 seconds, for example. Thus, there is need for simultaneous sealing and cutting to shorten the time required for an electrosurgical procedure.

Sealing and Cutting Signals

Figure 7:
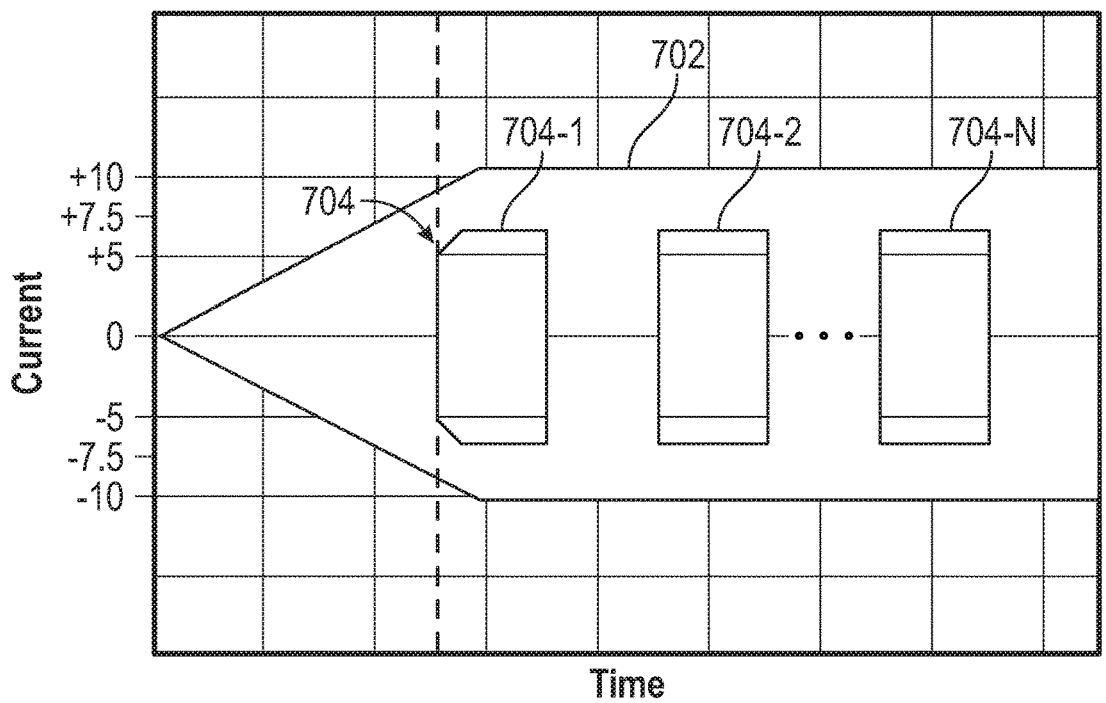
FIG. 7 is an illustrative signal timing diagram showing peak-to-peak current signal levels of simultaneous sealing and cutting signals in accordance with some embodiments.

FIG. 7 is an illustrative signal timing diagram showing example peak-to-peak current signal levels of simultaneous sealing and cutting signals in accordance with some embodiments. It will be appreciated that the drawing is illustrative and current level units and time units are arbitrary and for illustrative purposes only. The peak-to-peak current value of the RF sealing current signal 702 is greater than the peak-to-peak current value of the RF cutting current signal pulses 704-1 to 704-N. The sealing signal 702 is provided as a continuous RF signal. Whereas, the cutting signal 704 is provided in discrete RF signal pulses 704-1 to 704-N during discrete time intervals with a dead signal dwell time delay between each pulse during which no cutting signal is provided. Each RF signal pulse includes an RF cutting signal imparted continuously during the pulse time interval. Each dead signal dwell time delay includes a time interval during which no RF cutting signal is imparted. As explained below with reference to FIGS. 9A-9B, the number of cutting pulses may vary as required to achieve a satisfactory cut based upon a measure of impedance between the set of cut electrodes 510, 512. The sealing and cutting signals provide substantially the same power, and therefore, while the sealing signal current level is greater than the cutting signal current level, the sealing signal voltage level (not shown) is less than the cutting signal voltage level (not shown).

Control of Sealing and Cutting Signals

Figure 8:
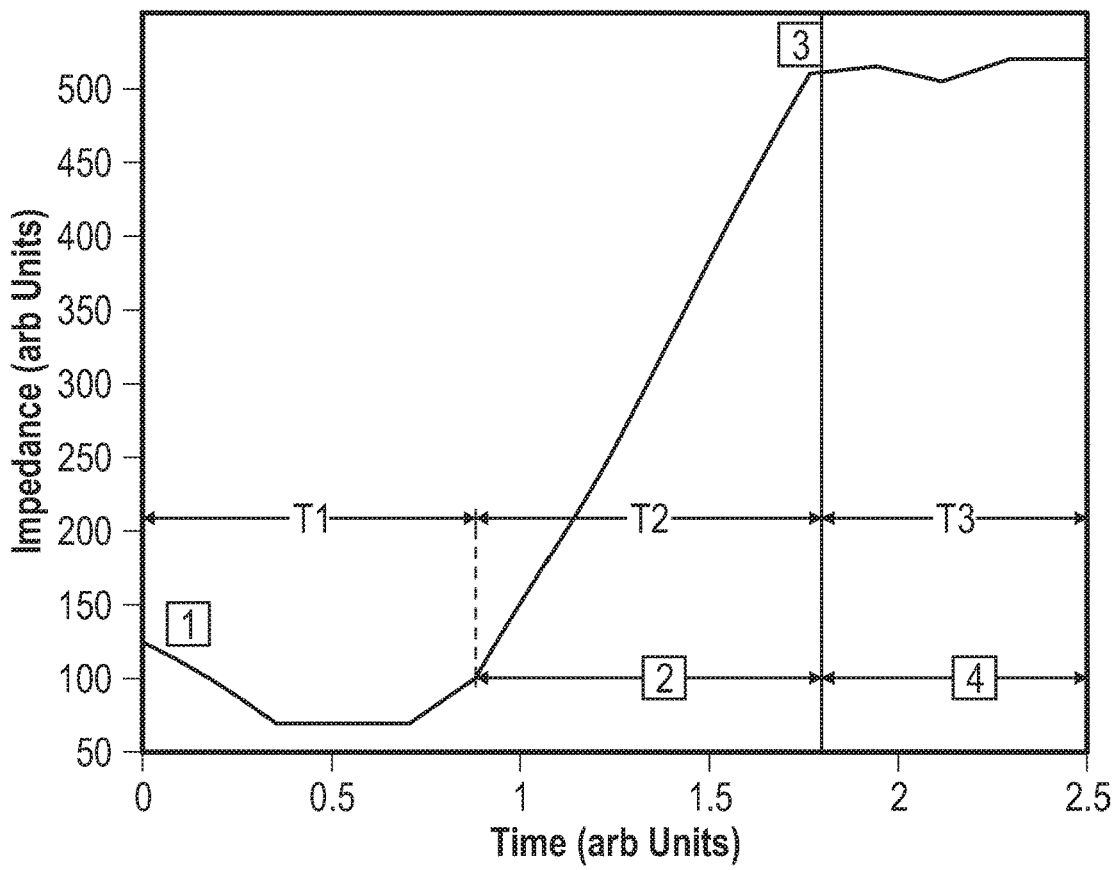
FIG. 8 is an illustrative example impedance versus time diagram representing a process to independently control sealing and cutting of biological tissue during simultaneous tissue sealing and tissue cutting activities in accordance with some embodiments.

FIG. 8 is an illustrative example impedance versus time diagram representing a process to independently control sealing and cutting of biological tissue during simultaneous tissue sealing and tissue cutting activities in accordance with some embodiments. It will be understood that the impedance values and time units indicated in the drawing are arbitrary and for the purpose of illustration. During a first time interval T1, starting at time t=0, the sealing stage 502 produces a sealing signal having a sealing signal voltage level. During the first time interval T1, the current and voltage measured between the set of sealing electrodes 506, 508 may be used to determine impedance between them. The monitored voltage and current between the sealing electrodes 506, 508 indicates impedance of biological tissue captured between the first and second jaws 602, 604 as shown in FIG. 6B, for example. Impedance may indicate tissue moisture content, for example. In general, tissue moisture content should be low enough to allow a suitable voltage and current density to be delivered to start cutting. The second micro-controller 562 is configured to cause the second output transformer 550 to produce the cutting signal based at least in part upon the impedance between the sealing electrodes 506, 508 reaching a pre-determined start-cutting threshold. During a second time interval T2, starting in the example at approximately time t=0.9, when the impedance between the sealing electrodes 506, 508 reaches a pre-determined start-cutting threshold, the cutting stage 504 produces the cutting signal. During the second time interval T2, the sealing stage 502 continues to produce the sealing signal while the cutting stage 504 simultaneously produces the cutting signal. As explained above with reference to the timing diagram of FIG. 7, although the sealing signal and the voltage signal are in-phase with each other, the sealing signal ordinarily has a lower peak-to-peak voltage than the cutting signal because a higher voltage generally is required to cut as explained above. During the second time interval T2, voltage and current measured between the set of sealing electrodes 510, 512 may be used to determine impedance between them. The first micro-controller 532 is configured to cause the first output transformer 520 to initiate a dwell mode in which the sealing signal is produced by the first output transformer for an additional pre-determined third time interval T3, based at least in part upon the impedance between the sealing electrodes 510, 512 reaching a pre-determined stop-sealing threshold indicating a predetermined tissue level, for example. At an approximate time of t=1.8 in the example, when the impedance between the sealing electrodes 510, 512 reaches pre-determined stop-sealing threshold, the sealing stage 502 enters the dwell mode in which the seal stage 502 continues to deliver the sealing signal for the additional pre-determined third time interval, which in the example, extends to approximately t=2.5, and then first micro-controller 532 causes the sealing stage 502 to halt the sealing signal. The cutting stage 504 may continue to produce the cut signal for a predetermined time interval (not shown), following which the second micro-controller 562 causes the cutting stage 504 to halt the cutting signal. Persons skilled in the art will appreciate that a lower impedance indicates presence of moisture which indicates presence of tissue still present between cut electrodes. A higher impedance indicates absence/reduction of moisture, which indicates absence/reduction of tissue between the electrodes, which indicates absence/reduction of tissue between the electrodes and/or a clean cut. Alternatively, in some embodiments, at the end of the fourth time interval in response to the current and voltage measured between the set of cutting electrodes 510, 512 indicating that impedance between them is less than a stop-cutting impedance threshold, the second micro-controller 562 may initiate additional cutting signal pulses to ensure satisfactory cutting of the biological tissue.

In some embodiments, the start cutting impedance threshold is less than the initiate dwell time impedance threshold and the stop cutting impedance threshold is greater than the initiate dwell time impedance threshold. In particular, for example, in some embodiments, a typical start cutting impedance threshold may be in a range 20-200 ohms, a typical initiate dwell time impedance threshold may be in a range 150-500 ohms, and a typical stop cutting impedance threshold may be in a range 500-2000 ohms. In accordance with some embodiments, a start cutting impedance is measured across seal electrodes and dwell time impedance threshold is also measured across seal electrodes. However, a stop cutting impedance will be measured across cut electrodes.

In alternative embodiments a phase angle between voltage, current or power delivered between the first and second jaws may also be used to determine a start-cutting threshold and a stop-sealing threshold. This alternative approach allows the reactive impedance to be considered, which generally is lower as the start of a seal and increases as the tissue dessicates.

Figure 9A:
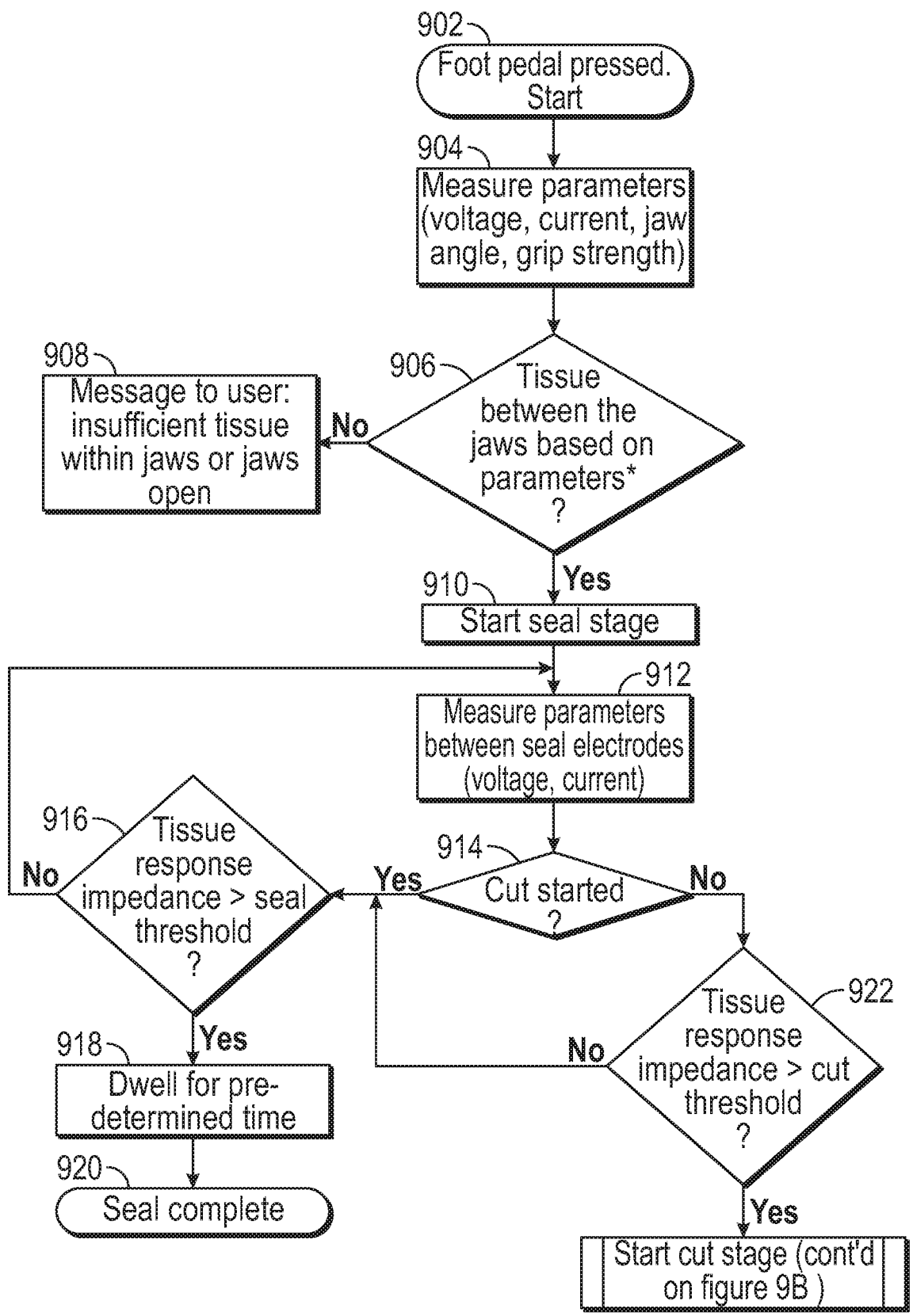
FIGS. 9A-9B are illustrative flow diagrams representing a first process to perform simultaneous sealing and cutting activities in accordance with some embodiments.
Figure 9B:
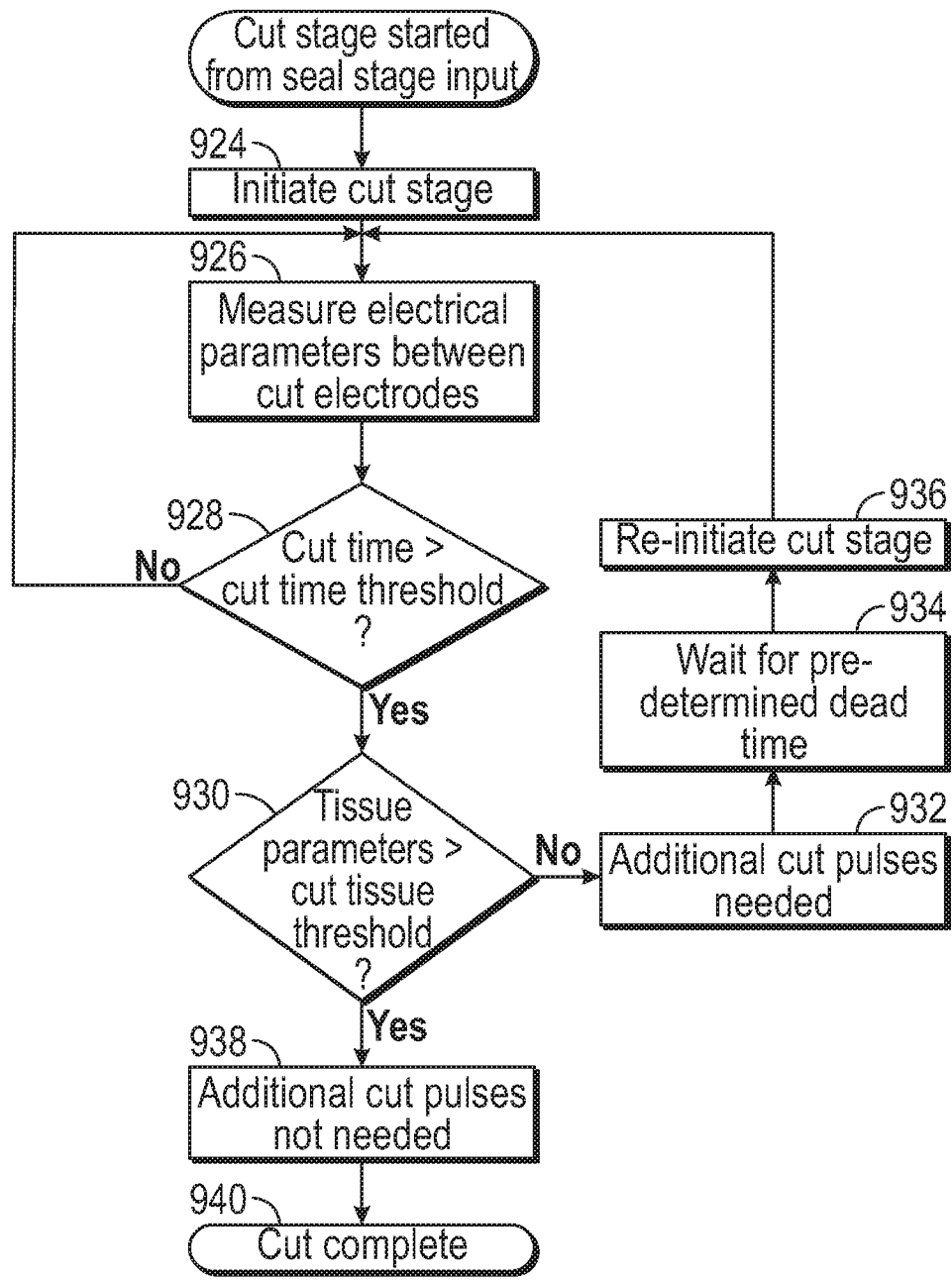

FIGS. 9A-9B are illustrative flow diagrams representing a first process to perform simultaneous sealing and cutting activities in accordance with some embodiments. The first and second micro-controllers 532, 562 and the main controller 572 may be configured with instructions to cause the first and second stages 502, 504 of the electrosurgical system 500 of FIG. 1 to perform the simultaneous sealing and cutting activities. At block 902, user input is received at a foot pedal UI actuator, for example, indicating a user command to start an electrosurgical procedure. At block 904, one or more bite parameters are measured including at least one of a test voltage and/or current between the sealing or cutting electrodes, jaw angle and jaw grip strength. A test signal may be provided between the sealing or cutting electrodes to produce the test voltage or current. The jaws 602, 604 may be configured with sensors (not shown) to determine jaw angle and grip force. At decision block, 906, a determination is made as to whether biological tissue is appropriately grasped between the jaws. At block 908, in response to a determination that tissue is not properly disposed between the jaws, a message is provided to the user via the UI to indicate insufficient or inappropriately positioned tissue between the jaws, for example.

At block 910, the first micro-controller 532 starts a sealing activity in response to a determination that tissue is properly disposed between the jaws 602, 604. The sealing activity includes the sealing stage providing a sealing signal to the set of sealing electrodes 506, 508 to impart a sealing signal within tissue 618 disposed between the first and third sealing surfaces 606, 610 and transmission of the sealing signal within tissue disposed between the second and fourth sealing surfaces 608, 612. At block 912, the first voltage and current monitoring circuit 530 monitors voltage and current at the set of sealing electrodes 506, 508. At decision block 914, the first micro-controller 532 determines whether the second micro-controller 562 has started to impart the cutting signal.

At decision block 916, in response to a determination that the cutting signal has started, the first micro-controller determines whether the monitored current and voltage between the set of sealing electrodes is greater than a stop-sealing impedance threshold. In response to the monitored impedance not reaching the stop-sealing impedance threshold, control returns to block 912 and current and voltage monitoring continues. At block 918, in response to the monitored impedance reaching the stop-sealing impedance threshold, the first microcontroller continues to propagate the sealing signal for a pre-determined sealing signal dwell time interval (T3). At block 920, at the end of the sealing signal dwell time interval, the first micro-controller halts the sealing process.

At decision block 922, in response to a determination that the cutting signal has not started, the second micro-controller 562 determines whether the monitored voltage and current between the set of sealing electrodes 506, 508 indicates an impedance greater than a start-cutting impedance threshold. Control flows to decision block 916 in response to a determination that the impedance between the set of sealing electrodes is not greater than a start-cutting impedance threshold. At block 924 the second micro-controller 562 starts a cutting activity in response to an indication that the tissue impedance has reached the start-cutting threshold. The cutting activity includes the cutting stage providing a cutting signal to the set of cutting electrodes 510, 512 to impart a cutting signal within tissue 618 disposed between the first and second cutting surfaces 610, 612 and 614. At block 926, the second voltage and current monitoring circuit 560 monitors voltage and current at the set of cutting electrodes 510, 512. At decision block 928, the second micro-controller 562 determines whether the cut time exceeds a cut-time threshold. In response to a determination that the cut-time threshold has not been reached, control flows back to block 926. At decision block 930, in response to a determination that the cut-time threshold has been reached, the second micro-controller 562 determines whether the monitored impedance between the set of cutting electrodes 510, 512 is greater than a stop-cutting impedance threshold. At block 932, in response to a determination that the impedance between the set of cutting electrodes 510, 512 is not greater than a stop-cutting impedance threshold, the second microcontroller 562 determines that additional cut-pulses are required to complete the cut. In accordance with some embodiments, the second micro-controller 562 determines the number of additional cut pulses to be provided based upon At block 934, the second micro-controller delays initiation of the additional cut pulses for a pre-determined dead time delay time during which no cutting signal is provided to allow the plasma to dissipate, and a new discharge be created at subsequent pulses, which can prevent a discharge from hanging at one specific location rather than making a complete cut. At block 936, following the delay, the second micro-controller re-initiates the cutting signal and control flows back to block 926. At decision block 938, in response to a determination that the cut-time threshold has been reached, the second-micro-controller 562 determines that additional cut pulses are not needed. At block 940, the second micro-controller 562 halts the cutting process.

In some embodiments, thresholds used to initialize dwell within seal output stage and initialize cut output stage start may be varied based upon jaw angle, grip force or other similar measurements. Measurements such as jaw angle and grip force can provide additional information on the status of tissue between the jaws. For example, a reduction in jaw angle implies loss of moisture or tissue desiccation or a clean cut Moreover, the timing of the cut output stage and seal output stage can be varied based on jaw angle, grip force or other similar measurements.

Furthermore, in some embodiments, instead of performing a single cut sequence with a predefined time, multiple shorter cut activations may be performed, with a period of dead time being introduced between each shorter activation. This can result in more reliable cutting performance, since the starting, stopping and restarting the sequence is more likely to vaporize residual tissue strands at the cut electrode that could cause an incomplete cut. Also, it may be desirable to suspend the activation of the seal sequence for some predetermined time to allow the tissues to cool and any vapor barrier between the tissue cutting surface and the tissue to dissipate, prior to starting the cut activation. This may result in a more uniform cut discharge and improved cut performance. Moreover, when the cut activation is terminated, it also may be desirable to suspend the seal activation for a predefined period of time, to allow the tissue to recover from the energy delivered during the cut activation, and allow a more accurate measurement of the electrical parameters being used to determine when the sealing sequence should advance to the next stage of the sequence. It will be appreciated that seal and cut signals are provided independently and in some situations, the seal signal may always end after the cut signal ends.

Figure 10:
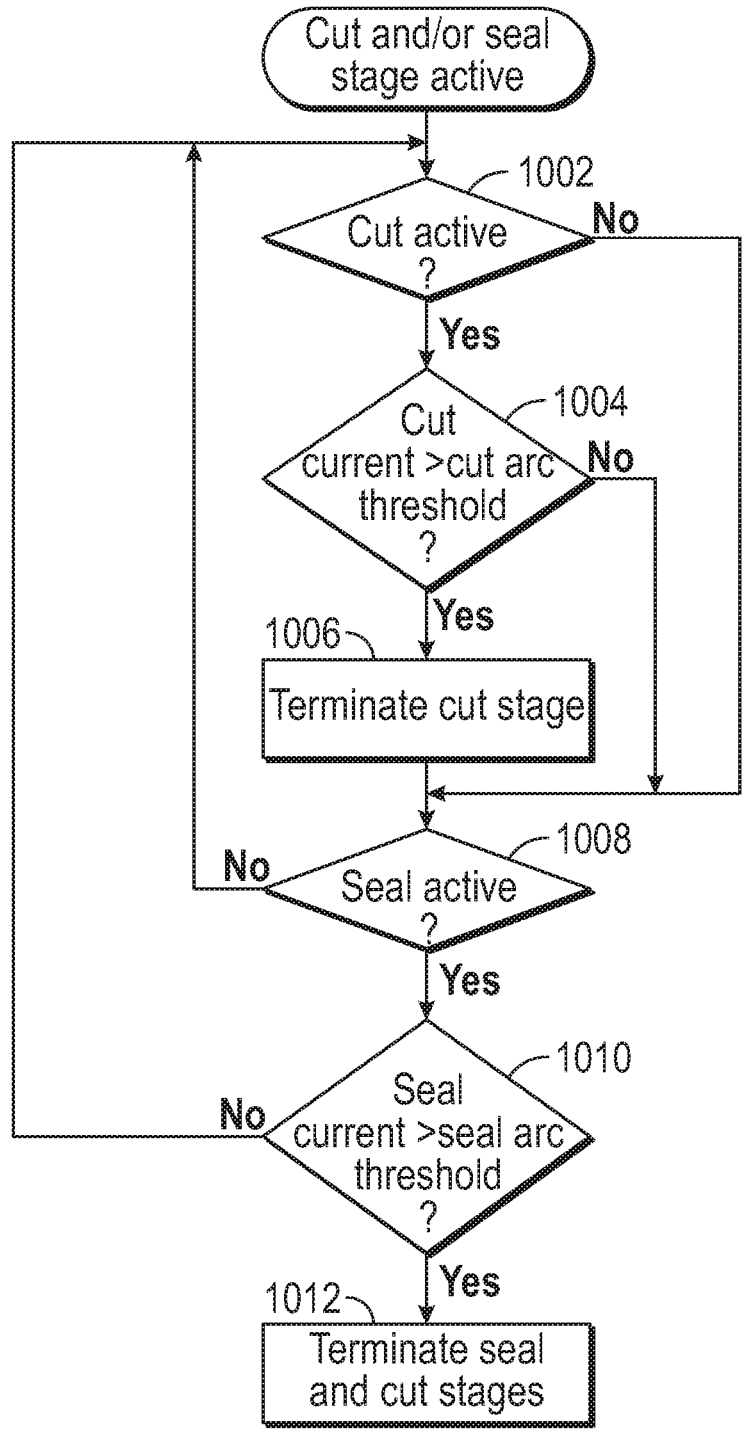
FIG. 10 is an illustrative flow diagram representing a second process to suppress arcs during simultaneous sealing and cutting activities in accordance with some embodiments.

FIG. 10 is an illustrative flow diagram representing a second process to suppress arcs during simultaneous sealing and cutting activities in accordance with some embodiments. The first and second micro-controllers 532, 562 and the main controller 572 may be configured with instructions to cause the first and second stages 502, 504 of the electrosurgical system 500 of FIG. 1 to perform the simultaneous sealing and cutting activities. Decision block 1002 determines whether the cutting signal is active. In response to a determination that the cutting signal is active, at decision block 1004 the second micro-controller 562 determines whether the monitored current between the set of cutting electrodes 510, 512 is greater than a cut arc threshold. At block 1006, in response to a determination that the monitored current between the set of cutting electrodes 510, 512 is greater than a cut arc threshold, the second micro-controller 562 halts the cutting signal. Control flows to decision block 1008 following block 1004, or following a determination at decision block 1002 that the cut signal is not active, or following a determination at decision block 1004 that the monitored current between the set of cutting electrodes 510, 512 is not greater than a cut arc threshold. Decision block 1008 determines whether the sealing signal is active. In response to a determination that the sealing signal is active, at decision block 1010 the first micro-controller 532 determines whether the monitored current between the set of sealing electrodes 506, 508 is greater than a seal arc threshold. At block 1012, in response to a determination that the monitored current between the set of sealing electrodes 506, 508 is greater than a seal arc threshold, the first micro-controller 532 halts the sealing signal and the second micro-controller 562 halts the cutting signal. It will be appreciated that cutting without sealing may result in bleeding, which is a reason to halt both cutting and sealing in response to a seal arc but not in response to a cut arc. Control flows to decision block 1002 following a determination at decision block 1008 that the seal signal is not active or following a determination at decision block 1010 that the monitored current between the set of cutting electrodes 510, 512 is not greater than a seal arc threshold.

Figure 11:
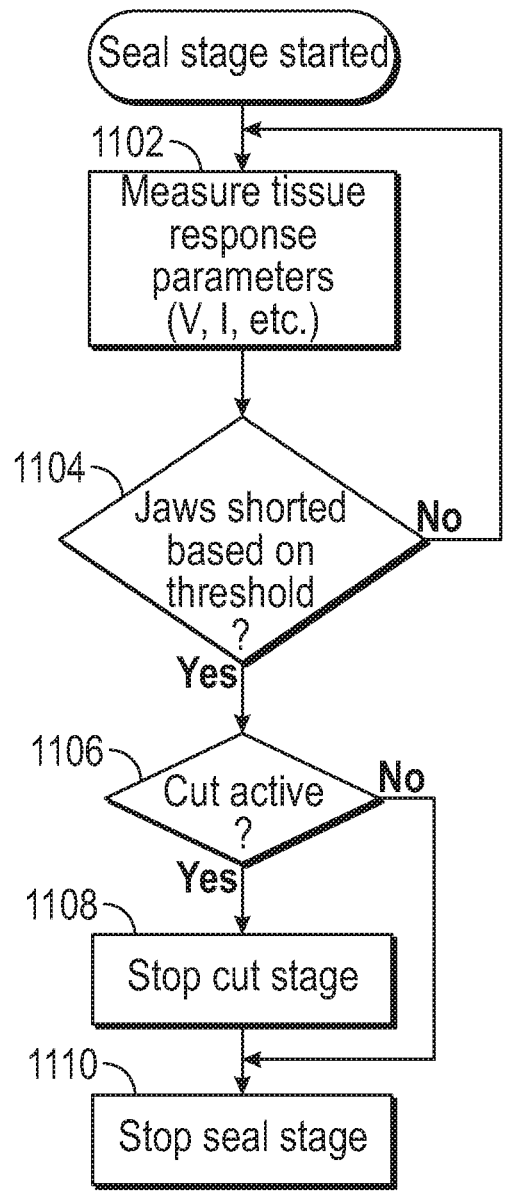
FIG. 11 is an illustrative flow diagram representing a third process to halt sealing and cutting activity in response to absence of biological tissue between the tissue sealing surfaces in accordance with some embodiments.

FIG. 11 is an illustrative flow diagram representing a third process to halt sealing and cutting activity in response to absence of biological tissue between the tissue sealing surfaces in accordance with some embodiments. The first and second micro-controllers 532, 562 and the main controller 572 may be configured with instructions to cause the first and second stages 502, 504 of the electrosurgical system 500 of FIG. 1 to perform the simultaneous sealing and cutting activities. The third process occurs while the sealing signal is active. At block 1102, the first voltage and current monitoring circuit monitors current and voltage between the set of sealing electrodes 506, 508. At block 1104, the first micro-controller 532 determines whether the monitored voltage and current between the set of sealing electrodes 506, 508 indicates direct electrical contact between any of the tissue sealing surfaces 606-612, i.e. between the first and third tissue sealing surfaces 606, 610 or between the second and fourth tissue sealing surfaces 608, 612. Direct contact between the tissue sealing surfaces, which may cause a short circuit, may result from an absence of biological tissue between the sealing surfaces. Control flows back to block 1102 in response to a determination that the monitored voltage and current between the set of sealing electrodes 506, 508 does not indicate direct electrical contact between any of the tissue sealing surfaces 606-612. At decision block 1106, in response to a determination that the monitored voltage and current between the set of sealing electrodes 506, 508 does indicate direct electrical contact between any of the tissue sealing surfaces 606-612, the second micro-controller 562 determines whether the cutting signal is active. At block 1108, in response to a determination that the cutting signal is active, the second micro-controller 562 halts the cutting signal. At block 1110, following block 1108 or following a determination at block 1106 that the cutting stage is not active, the first micro-controller 532 halts the sealing signal. It will be appreciated that the high energy delivered from an arc could damage the instrument itself, and make it ineffective; e.g. poor sealing performance.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein. The above description is presented to enable any person skilled in the art to create and use electrosurgical signals to simultaneously seal and cut biological tissue. Various modifications to the embodiments will be readily apparent to those skilled in the art, and the generic principles defined herein may be applied to other embodiments and applications without departing from the scope of the invention. In the preceding description, numerous details are set forth for the purpose of explanation. For example, the electrosurgical signal generator circuit may include a single processor configured with instructions to run separate processes to control the sealer stage and the dissection stage. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. A method to seal and cut biological tissue comprising:
   imparting a continuous alternating current (AC) sealing signal between a set of sealing electrodes;
   determining impedance of biological tissue disposed between the set of sealing electrodes while the AC sealing signal is imparted between the set of sealing electrodes;
   in response to the impedance of biological tissue disposed between the sealing electrodes reaching a first impedance threshold value, imparting an AC cutting signal that includes imparting a discrete AC cutting signal pulse between a set of cutting electrodes during each of one or more discrete AC cutting signal pulse intervals, while the AC sealing signal is imparted between the sealing electrodes;
   determining the impedance of the biological tissue disposed between the set of sealing electrodes while the AC cutting signal is imparted between the set of cutting electrodes;
   halting the AC sealing signal between the set of sealing electrodes after waiting a predetermined sealing signal dwell time after determining that the impedance of the biological tissue disposed between the set of sealing electrodes has reached a second impedance threshold value, the second impedance threshold value being higher than the first impedance threshold value; and
   after the AC sealing signal has been halted, determining whether the impedance of biological tissue disposed between the set of sealing electrodes has reached a third impedance threshold value, the third impedance threshold value being higher than the second impedance threshold value,
   wherein, if the impedance of the biological tissue disposed between the set of sealing electrodes has reached the third impedance threshold value, the AC cutting signal is halted, and
   wherein, if the impedance of the biological tissue disposed between the set of sealing electrodes has not reached the third impedance threshold value, the AC cutting signal is stopped for a predetermined delay time and re-initiated after the predetermined delay time.

2. The method of claim 1,
   wherein one or more of the discrete AC cutting signal pulse intervals occurs after the act of halting the AC sealing signal.

3. The method of claim 1,
   wherein the AC sealing signal is in-phase with the AC cutting signal.

4. The method of claim 1,
   wherein the act of imparting the AC sealing signal between the set of sealing electrodes and the act of imparting the AC cutting signal between the set of cutting electrodes includes imparting the AC sealing signal and imparting the AC cutting signal to at least one electrode that is shared in common between the set of sealing electrodes and the set of cutting electrodes.

5. The method of claim 1,
   wherein imparting the AC cutting signal between the set of cutting electrodes includes continuously imparting the AC cutting signal between the set of cutting electrodes during each of multiple discrete AC cutting signal pulse intervals.

6. The method of claim 1,
   wherein imparting the AC cutting signal between the set of cutting electrodes includes continuously imparting the AC cutting signal between the set of cutting electrodes during each of multiple discrete AC cutting signal pulse intervals; further including:
   adjusting a number of discrete AC cutting signal pulses based upon an impedance value of biological tissue disposed between the set of cutting electrodes.

7. The method of claim 1,
   wherein imparting the AC cutting signal between the set of cutting electrodes includes continuously imparting the AC cutting signal between the set of cutting electrodes during each of multiple discrete AC cutting signal pulse intervals;
   further including:
   adjusting a seal dwell time after an occurrence of one or more of the discrete AC cutting signal pulse intervals based upon an impedance value of biological tissue disposed between the set of sealing electrodes.

8. The method of claim 1 further including:
   determining the impedance of the biological tissue disposed between the set of sealing electrodes while the AC cutting signal is imparted between the set of cutting electrodes; and
   halting the AC sealing signal and the AC cutting signal in response to the impedance of the biological tissue disposed between the set of sealing electrodes reaching a seal arc threshold value.

9. The method of claim 1 further including:
   determining the impedance of the biological tissue disposed between the set of sealing electrodes while the AC cutting signal is imparted between the set of cutting electrodes;
   determining impedance of biological tissue disposed between the set of cutting electrodes while the AC sealing signal is imparted between the set of sealing electrodes; and
   halting the AC cutting signal while continuing to impart the AC sealing signal in response to the impedance of the biological tissue disposed between the set of cutting electrodes reaching a cutting arc threshold value and the impedance of the biological tissue disposed between the set of sealing electrodes not reaching a seal arc threshold value.

10. The method of claim 1, further including:
    wherein the set of sealing electrodes includes an active sealing electrode and a shared return electrode;
    wherein the set of cutting electrodes includes an active cutting electrode and the shared return electrode;

wherein a peak-to-peak voltage of the AC cutting signal is different from a peak-to-peak voltage of the sealing signal;
wherein the active sealing electrode is electrically coupled to first and second electrically conductive tissue sealing surfaces formed in a working surface of a first jaw;
wherein the active cutting electrode is electrically coupled to an electrically conductive tissue cutting surface formed on the working surface of the first jaw, located between the first and second electrically conductive tissue sealing surfaces;
wherein the shared return electrode is electrically coupled to third and fourth electrically conductive sealing surfaces formed in a working surface of a second jaw so as to align with the first and second electrically conductive tissue sealing surfaces, when the first and second jaws are in a closed position;
wherein at least one of the first and second jaws is mounted to rotatably pivot about a pivot axis between an open position in which the first and second jaws are spaced apart from each other and the closed position a second position for grasping tissue therebetween.

11. The method of claim 10,
wherein the working surface of the second jaw includes an insulative surface located between the third and fourth electrically conductive sealing surfaces so as to align with the first electrically conductive tissue cutting surface when the first and second jaws are in the closed position.

12. The method of claim 1, wherein the first impedance threshold value is determined based on a first phase angle between a voltage or a current delivered between two electrodes included in the set of sealing electrodes, wherein the two electrodes are associated with a first jaw and a second jaw.

13. The method of claim 1, wherein the first impedance threshold value is determined based on at least one of a jaw angle between a first jaw and a second jaw or a grip force applied by the first jaw and the second jaw.

14. The method of claim 1, wherein imparting the AC cutting signal achieves a plasma discharge, and the predetermined delay time is configured to be sufficient to allow the plasma discharge to dissipate before the AC cutting signal is re-initiated.

15. The method of claim 1, further comprising determining whether a cut time associated with imparting the AC cutting signal exceeds a cut-time threshold, and when the cut time has reached the cut-time threshold, determining the impedance of the biological tissue disposed between the set of sealing electrodes.

16. An electrosurgical system comprising:
an electrosurgical signal generator sealing stage to provide an AC sealing signal on a set of sealing electrodes;
an electrosurgical signal generator cutting stage to provide an AC cutting signal on a set of cutting electrodes;
wherein the set of sealing electrodes and the set of cutting electrodes share at least one electrode in common;
at least one controller configured to determine impedance of biological tissue disposed between the set of sealing electrodes while the AC sealing signal is imparted between the set of sealing electrodes;
wherein the controller is configured to control the electrosurgical signal generator sealing stage to impart a continuous AC sealing signal between the set of sealing electrodes, and in response to the impedance of the biological tissue disposed between the sealing electrodes reaching a first impedance threshold value, to control the electrosurgical signal generator cutting stage to impart an AC cutting signal that includes imparting a AC cutting signal pulse between a set of cutting electrodes during each of one or more discrete AC cutting signal pulse intervals, while the AC sealing signal is imparted between the sealing electrodes;
wherein the at least one controller is configured to determine the impedance of the biological tissue disposed between the set of sealing electrodes while the AC cutting signal is imparted between the set of cutting electrodes;
wherein the at least one controller is configured to control the electrosurgical signal generator sealing stage to halt the AC sealing signal between the set of sealing electrodes after waiting a predetermined sealing signal dwell time after determining that the impedance of the biological tissue disposed between the set of sealing electrodes has reached a second impedance threshold value, the second impedance threshold value being higher than the first impedance threshold value;
wherein the at least one controller is configured to, after the AC sealing signal has been halted, determine whether the impedance of the biological tissue disposed between the set of sealing electrodes has reached a third impedance threshold value, the third impedance threshold value being higher than the second impedance threshold value,
wherein, if the impedance of the biological tissue disposed between the set of sealing electrodes has reached the third impedance threshold value, the AC cutting signal is halted, and
wherein, if the impedance of the biological tissue disposed between the set of sealing electrodes has not reached the third impedance threshold value, the AC cutting signal is stopped for a predetermined delay time and re-initiated after the predetermined delay time.

17. The electrosurgical system of claim 16,
wherein the AC sealing signal and the AC cutting signal are in-phase.

18. The electrosurgical system of claim 16,
wherein the electrosurgical signal generator cutting stage is configured to adjust a number of cutting signal pulses based upon an impedance value of biological tissue disposed between the set of cutting electrodes.

19. The electrosurgical system of claim 16,
wherein the electrosurgical signal generator cutting stage is configured to provide the AC cutting signal in discrete pulse intervals; and
wherein the electrosurgical signal generator cutting stage is configured to adjust a dwell time between cutting signal pulses based upon an impedance value of biological tissue disposed between the set of sealing electrodes.

20. The electrosurgical system of claim 16, further including:
an instrument including a first jaw and a second jaw having opposed working faces and a pivot axis, wherein at least one of the first and second jaws is mounted to rotatably pivot about the pivot axis between an open position in which the first and second jaws are spaced apart from each other and a closed position a second position for grasping tissue therebetween;
wherein the set of sealing electrodes includes an active sealing electrode and a shared return electrode;
wherein the set of cutting electrodes includes an active cutting electrode and the shared return electrode;

wherein a peak-to-peak voltage of the AC cutting signal is different from a peak-to-peak voltage of the AC sealing signal;

wherein the first jaw includes a working surface that includes first and second electrically conductive tissue sealing surfaces electrically coupled to the active sealing electrode;

wherein the working surface of the first jaw includes an electrically conductive cutting surface, located between the first and second electrically conductive tissue sealing surfaces, electrically coupled to the active cutting electrode; and wherein the second jaw includes a working surface that includes third and fourth electrically conductive tissue sealing surfaces, located so as to align with the first and second electrically conductive tissue sealing surfaces when the first and second jaws are in the closed position, electrically coupled to the shared return electrode.

21. The electrosurgical system of claim 20, wherein the working surface of the second jaw includes an insulative surface located between the third and fourth electrically conductive tissue sealing surfaces so as to align with the first electrically conductive tissue cutting surface when the first and second jaws are in the closed position.

* * * * *